(12) United States Patent
Roshkovan

(10) Patent No.: US 10,709,532 B2
(45) Date of Patent: Jul. 14, 2020

(54) ATRAUMATIC HIGH-VOLUME DENTAL EVACUATION TIP

(71) Applicant: Igor Roshkovan, Los Angeles, CA (US)

(72) Inventor: Igor Roshkovan, Los Angeles, CA (US)

(*) Notice: Subject to any disclaimer, the term of this patent is extended or adjusted under 35 U.S.C. 154(b) by 218 days.

(21) Appl. No.: 16/024,878

(22) Filed: Jul. 1, 2018

(65) Prior Publication Data
US 2020/0000565 A1 Jan. 2, 2020

(51) Int. Cl.
| | |
|---|---|
| A61C 17/06 | (2006.01) |
| A61C 17/14 | (2006.01) |
| A61C 17/08 | (2006.01) |
| A61M 1/00 | (2006.01) |

(52) U.S. Cl.
CPC ............. *A61C 17/08* (2019.05); *A61M 1/008* (2013.01)

(58) Field of Classification Search
CPC . A61C 17/08; A61C 3/00; A61C 1/00; A61M 1/008; A61M 2210/0625; A61M 2210/0643; A61M 1/0058; A61M 3/0279; A61M 25/0068; A61M 25/0067
See application file for complete search history.

(56) References Cited

U.S. PATENT DOCUMENTS

| | | |
|---|---|---|
| 3,460,255 A | 8/1969 | Hutson |
| 4,068,664 A | 1/1978 | Russell |
| 4,487,600 A | 12/1984 | Brownlie |
| 4,695,253 A | 9/1987 | Tysse |
| 4,767,404 A | 8/1988 | Renton |
| 4,867,747 A * | 9/1989 | Yarger .................. A61M 1/008 604/263 |
| 5,425,637 A | 6/1995 | Whitehouse |
| 5,489,276 A * | 2/1996 | Jamshidi ................ A61C 17/08 604/268 |
| 5,690,487 A | 11/1997 | Whitehouse |
| 5,741,134 A | 4/1998 | Davis |
| 6,183,254 B1 | 2/2001 | Cohen |
| 1,712,419 A1 | 2/2007 | Hasegawa |
| 8,556,872 B1 | 10/2013 | Hamman et al. |
| 9,532,857 B2 | 1/2017 | Ronto |

(Continued)

FOREIGN PATENT DOCUMENTS

| | | |
|---|---|---|
| EP | 1700578 A1 | 9/2006 |
| WO | WO-2019216028 A1 * | 11/2019 ............ A61M 25/00 |

*Primary Examiner* — Amy R Weisberg

(57) ABSTRACT

The embodiment provides a high-volume evacuation tip perforated with round shape apertures covered by vent shells with upgraded capability of capturing escaping saliva and surgical debris during dental operation, as well as its total mass flow capability with soft silicone rubber nozzle. The high-volume suction tip for dental procedures has a cylinder or tubular-shaped, having two open ends. Forward-facing end has a soft silicone rubber nozzle is round in shape reducing patient pain and discomfort due to contact of hard plastic suction with soft tissue of patient with several vertical milling cutters to improve maximum effectiveness of fluid absorption, preventing clogging a surgical aspirator and prevent traumatic absorption of the patient tongue. Posterior end has vertical cutting shape. The suction tip has increase impact force compare to similar suction tips without the plurality of apertures or with few of them.

12 Claims, 26 Drawing Sheets
(19 of 26 Drawing Sheet(s) Filed in Color)

(56) References Cited

U.S. PATENT DOCUMENTS

| | | |
|---|---|---|
| 2003/0017433 A1 | 1/2003 | Reiz |
| 2005/0096608 A1 | 5/2005 | Mannschedel |
| 2005/0197633 A1 | 9/2005 | Schwartz et al. |
| 2009/0136895 A1 | 5/2009 | Khalaf |
| 2010/0152707 A1 | 6/2010 | Morris |

* cited by examiner

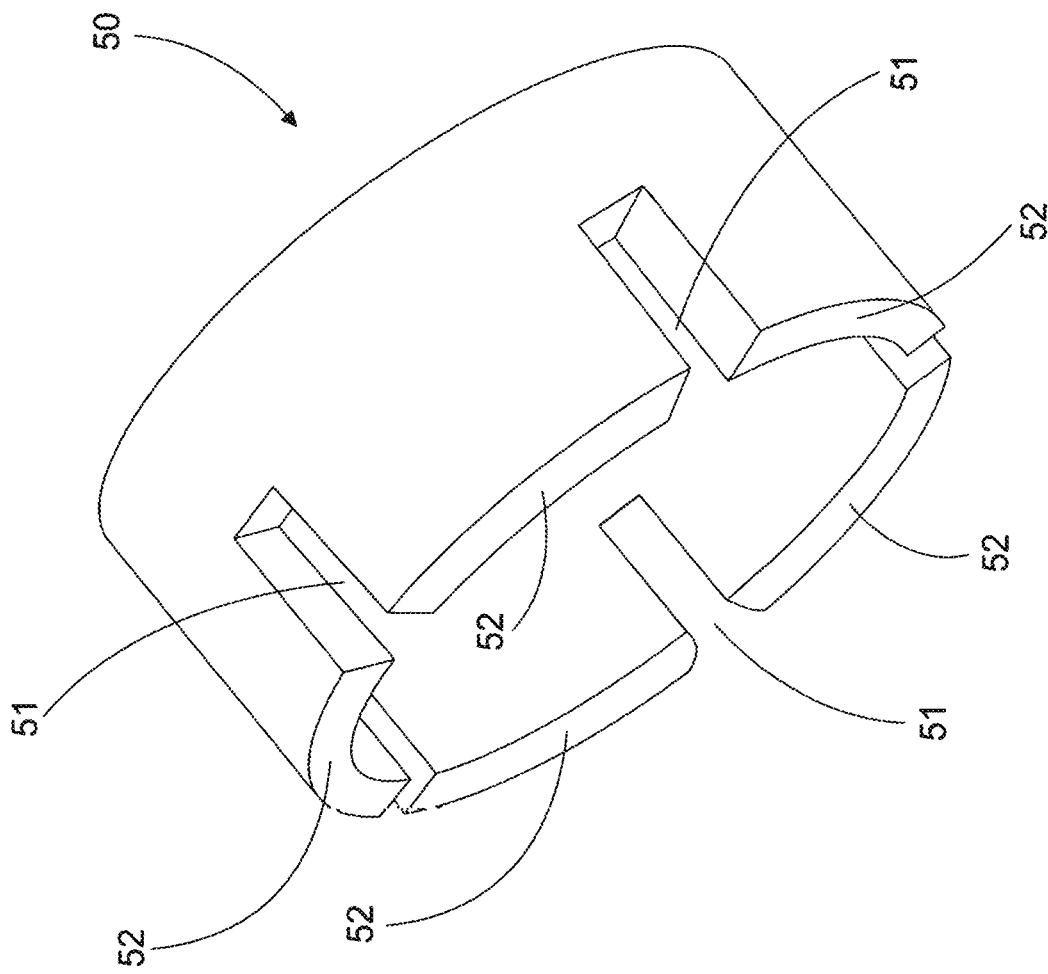

ATRAUMATIC HIGH-VOLUME DENTAL EVACUATION TIP

BACKGROUND-PRIOR ART

This disclosure concerns improved dental care for dental patients, and more to a novel high volume dental suction tip. This embodiment relates particularly to suction high-volume dental evacuation device having improved tip and has reference to the portion of suction device as an evacuation tip that is particularly adapted for dental use which allow for more efficient suctioning function.

The following is a tabulation of some prior art that presently appears relevant:

U.S. Patents

| Pat. No. | Kind Code | Issue Date | Patentee |
|---|---|---|---|
| 9,532,857 | B2 | 2017 Jan. 3 | Ronto |
| 8,556,872 | B1 | 2013 Oct. 15 | Hamman et al. |
| 4,867,747 | A | 1989 Sep. 19 | Yarger |
| 4,767,404 | A | 1988 Aug. 30 | Renton |

U.S. Patent Application Publications

| Publication Nr. | Kind Code | Publ. Date | Applicant |
|---|---|---|---|
| 20050197633 | A1 | 2005 Sep. 8 | Schwartz at el. |

Foreign Patent Documents

| Foreign Doc. Nr. | Cntry Code | Kind Code | Pub. Dt | Patentee |
|---|---|---|---|---|
| 1700578 | EP | A1 | 2006-09 | Hasegawa |

Oral high-volume suction devices such as those used in dentistry and generally well known. Oral suction high-volume tips have historically consisted of a rigid plastic or metal tube having a lumen formed in the center. They have had an oblique distal end the proximal end of the dental suction tip is configured to connect to a source of vacuum. All these devices are typically considered undesirable for patient and for dental stuff.

During dental procedure fluids such as saliva, water and surgical debris accumulate in the mouth of patient. Their removal is accomplished with a range of suction devices. Usually these devices include some tubes in a few different forms.

The water, saliva and surgical debris enter the wand through the open end. Previous designs of high-volume dental evacuation tips were not perfect. In fact, only front end was used in major designs and in some different designs were used additional flat apertures.

And this led to the fact that suction tip clogged, fluids splatter on the face of patients and dental office personnel. And in addition to these inconveniences hard plastic suction tip touches the soft tissue of patient's mouth and caused discomfort, irritations and pain, making suctioning ineffective or impossible to perform due the failed of structure design of suction tip. These designs have continued to present problems.

Based on these factors the presented embodiment takes into consideration to attend to these needs all the disadvantages inherent of the previous models that received patents.

Some suction devices of prior art are designed to drain fluids from a patient mouth. To the best of the applicants' knowledge none of the previously developed devices can attend to these need was described previously.

All previous prior arts can be divided into three groups:

The first group can include patents that described the design of dental suction tubes or high-volume suction tip with limited numerous flat apertures only, in different parts of cylinder shape of tube without silicone tip in the one end. This design of dental suctions with openings can easily become partially or completely clogged. An addition hard solid plastic tip can traumatized the delicate soft tissue of patient. These designs making suction ineffective due to decreased impact force.

In this group of prior art devices can include the following patents and applications:

U.S. Patents

| Pat. No. | Kind Code | Issue Date | Patentee |
|---|---|---|---|
| 9,532,857 | B2 | 2017 Jan. 3 | Ronto |
| 4,068,664 | A | 1978 Jan. 17 | Russell at el. |
| 4,695,253 | A | 1987 Sep. 22 | Tysse |
| 4,487,600 | A | 1984 Dec. 11 | Brownlie at el. |

U.S. Patents

| Pat. No. | Kind Code | Issue Date | Patentee |
|---|---|---|---|
| 4,867,747 | A | 1989 Sep. 19 | Yarger |
| 4,767,404 | A | 1988 Aug. 30 | Renton |
| 3,460,255 | A | 1969 Aug. 12 | Hutson |

U.S. Patent Application Publications

| Publication Nr. | Kind Code | Publ. Date | Applicant |
|---|---|---|---|
| 20050197633 | A1 | 2005 Sep. 8 | Schwartz at el. |

The second group contains patents that described the design of dental suction tubes or high-volume suction tip with one single flat aperture only, in different parts of cylinder shape of tube without silicone tip in the one end. This design of dental suctions with only one opening can easily become partially or completely clogged and patient can die due to aspiration by saliva, blood and debris. An addition hard solid plastic tip can traumatized the delicate soft tissue of patient previously noted. These designs have continued to present problems.

In this group of prior art devices can include the following patents and applications:

U.S. Patents

| Pat. No. | Kind Code | Issue Date | Patentee |
|---|---|---|---|
| 8,556,872 | B1 | 2013 Oct. 15 | Hamman et al. |

U.S. Patent Application Publications

| Publication Nr. | Kind Code | Publ. Date | Applicant |
|---|---|---|---|
| 20090136895 | A1 | 2009 May 28 | G. Khalaf |

And last third group contains patents and applications that described the design of dental suction tubes or high-volume suction with silicone tip in the one end only, without any orifices or apertures on the body of suction tip.

This design of dental suctions without apertures in the body of suction can easily become partially or completely clogged as mentioned before. This design making suction ineffective due to decreased impact force too.

The Prior Art List is

U.S. Patents

| Pat. No. | Kind Code | Issue Date | Patentee |
|---|---|---|---|
| 7,172,419 | B2 | 2007 Feb. 6 | Hasegawa |

Foreign Patent Documents

| Foreign Doc. Nr. | Cntry | Kind Code | Pub. Dt | Patentee |
|---|---|---|---|---|
| 1700578 | EP | A1 | 2006-09 | Hasegawa |

As a result, we need for high-volume dental suction which effectively suction any fluids, saliva, and surgical debris and which will not become easily blocked by debris. There is a need for a dental suction tip which has a necessary numbers of openings in with shells to improve effectiveness of suction forces to avoid blockage and greatly minimize trauma to patient.

BRIEF SUMMARY AND OBJECTS OF THE EMBODIMENT

In reaction to the complications and problems discussed herein, very effective and not traumatic high-volume dental evacuation tip is provided.

In one embodiment of the present disclosure is directed to a high volume dental suction tip, including a cylinder shape body with a function round shape apertures covered by vent shells and located on all surfaces in the entire length of tube and vacuum source silicone rubber tip end adapted to be used in dental procedures and configured to include all the advantages of invention, and to improve the drawbacks inherent therein.

However, apertures and vent shells can have different cross sections, such as rectangular, oval, triangular, circular etc.

Therefore, an item of present embodiment is to provide a new concept and value-added evacuation tip for collecting oral fluids and debris during dental procedures.

An advance object of the current invention is to provide a way that can enhanced of function a suction tip.

Additional object of the present invention is to offer an evacuation forward-facing end tip that has a soft silicone wedges rubber nozzle is round in shape, with several vertical milling cutters with capability of eliminating the possibility of causing discomfort and pain to soft tissues patient's mouth. An addition the shape of silicone silic nozzle with several slotted apertures of this embodiment is constructed so as to prevent pain and discomfort of patient and increasing suction mass flow forces at least 30 percent more than a similar evacuation tips made from the same material but having no nozzle with wedges and slotted openings, preventing dogging a surgical aspirator.

More over this particular shape of $silico_{ne}$ wedges nozzle totally prevent absorption of patient tongue into suction tip and cause trauma.

It is also an object of the present embodiment is to provide an evacuation tip that has to be disposable and comfortable to use during the any procedures in dentistry and can use in medicine in general.

On the of above objects, in one aspect, the present invention provides an evacuation tip that is adapted to be used with upgraded capability of capturing escaping saliva, fluids and surgical debris during dental operation, as well as its total mass flow improved capability.

An addition also provided herein is a suction tip that has strong force at least up to 30 percent more than a similar suction dental tips made from same material but having no or few apertures without went shells. The evacuation tip has a cylindrical body perforated with apertures covered by vent shells located on all surfaces in the entire length of tube. However evacuation tip can have different cross sections, such as oval, circular, etc.

The evacuation tip contains a forward-facing end portion and a distal end portion. The first one end portion covers by soft silicone rubber nozzle, rounded in shape with several vertical milling cutters to improve maximum effectiveness of fluid absorption, preventing clogging a surgical aspirator and prevent discomfort suction of the patient tongue. Further the second end portion is connected to the evacuation system machine.

For a well accepting of the present embodiment, are set forth in the accompanying drawings and the explanation below. The descriptive matter in which there are demonstrated exemplary embodiments of the present invention.

The evacuation tip has a cylindrical body perforated with plurality of apertures with all have the same sizes covered by vent shells located on all surfaces in the entire length of tube. The function of apertures and vent shells are improve suction force at least 30% more than a similar suction tips made from same material but having no or few apertures without vent shells.

An addition present invention can be widely used in other medical fields such as general surgery, urology, pulmonology, orthopedic surgery, cardiology, etc.

REFERENCES CITED

U.S. Patents

| Pat. No. | Kind Code | Issue Date | Patentee |
| --- | --- | --- | --- |
| 3,460,255 | A | 1969 Aug. 12 | Hutson |
| 4,068,664 | A | 1978 Jan. 17 | Sharp et al. |
| 5,425,637 | A | 1995 Jun. 20 | Whitehouse et al. |
| 5,690,487 | A | 1997 Nov. 25 | Whitehouse et al. |
| 5,741,134 | A | 1998 Apr. 21 | Davis |
| 6,183,254 | B1 | 2001 Feb. 6 | Cohen |

U.S. Patent Application Publications

| Publication Nr. | Kind Code | Publ. Date | Applicant |
| --- | --- | --- | --- |
| 20030017433 | A1 | 2003 Jan. 23 | Reiz |
| 20050096608 | A1 | 2005 May 5 | Mannschedel et al. |
| 20100152707 | A1 | 2010 Jun. 17 | Morris et al. |

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 7 is a perspective view of the silicone wedges color of the of the high-volume dental evacuation tip of FIG. 1.

DRAWINGS—REFERENCE NUMERALS

Figure 1:
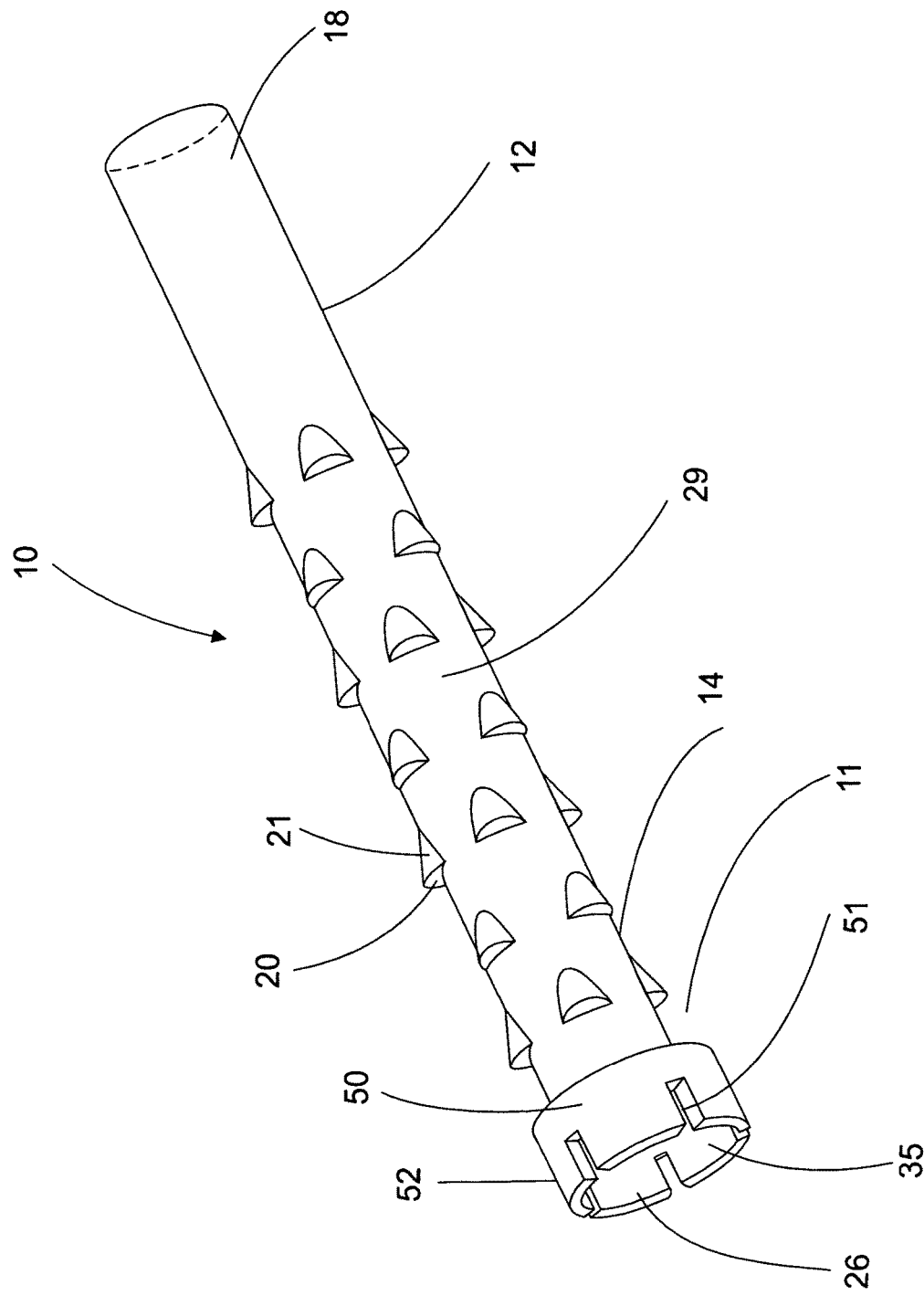
FIG. 1 is a perspective view of a high-volume dental evacuation tip that the present embodiment.
Figure 2:
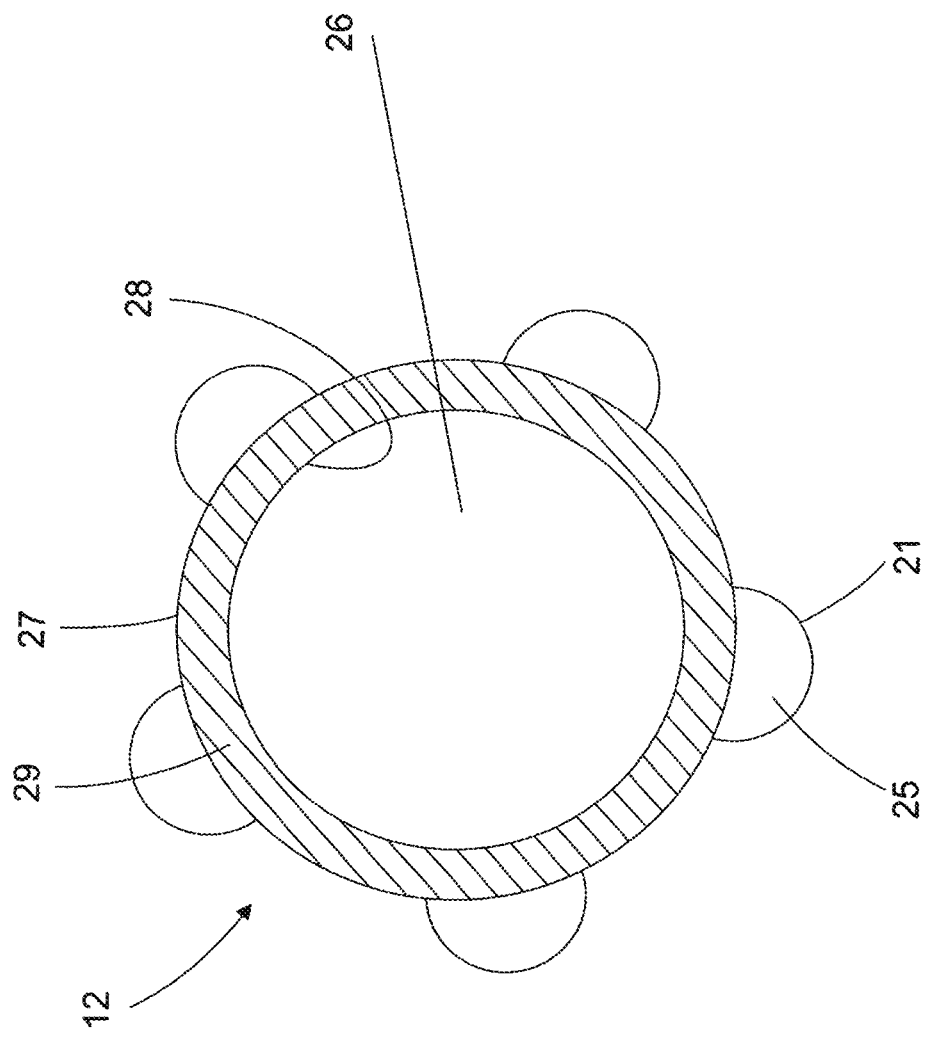
FIG. 2 is a cross-sectional view of the proximal portion of high-volume dental evacuation tip with present embodiment of FIG. 1.

10 High-volume dental evacuation suction tip
11 Forward-facing end
12 Proximal portion of tip
13 Longitudinal axis
14 Distal portion of tip
18 Posterior end
20 The apertures
21 The shell
22 The palatal wall of shell
23 The parietal wall of shell
24 Outer lip of shell
25 Outer wall of shell
26 Hollow interior
27 Outer surface
28 Inner surface
29 Outer wall of tip
30 Distal opening
35 Distal opening
50 The silicone wedges nozzle-color
51 Slotted openings
52 Silicone wedge

DETAILED DESCRIPTION OF THE PREFERRED EMBODIMENT

An embodiment of a high-volume dental evacuation tip 10 of the present invention as shown in FIGS. 1-7. Referring specifically to FIGS. 1, 2, 3, 6 and 7 the high-volume dental evacuation tip 10 includes a proximal portion of tip 12, a distal portion of tip 14 and forward-facing end 11. The proximal portion 12 and distal portion of tip 14 are preferably a cylinder or tubular-shaped in nature. In other embodiments, the cross section is rectangular, triangular, oval or circular. The proximal portion 12 includes a posterior end 18 with an opening and an outer wall of tip 29 having an outer surface 27 and an inner surface 28 (see FIG. 2). The proximal portion 12, and the entirety of the a high-volume evacuation tip has a substantially hollow interior 26 which allows passage of fluids such as saliva, water and surgical debris there through when suction device is applied to the tip 10. The plurality of apertures 20 cover by shells 21 extend radially outwardly from the outer surface 27 of the proximal portion 12 to the distal portion of the tip 14 (see FIGS. 1,3,4,5)

As a shown in FIGS. 1,2,4,5 the outer wall 29 has an outer surface 27 that has a plurality of apertures 20 therein covered by vent shells 21, each of which extend from the outer surface 27, through wall 29, to distal portion of tip 14. The plurality of apertures 20 cover by shells 21 extend radially outwardly from the outer surface 27 of the proximal portion 12 to the distal portion of the tip 14 (see FIGS. 1,3,4,5).

Preferably, a high-volume dental evacuation tip 10 contains at least 30 shell apertures. The apertures could be rectangular, oval, triangular, circular, or similar shaped.

The distal portion 14 of the tube 10 is formed of at least one wall 29 which is connected to the proximal portion 12. Thus, the distal portion 14 is in fluid communication with the proximal portion 12. Distal portion 14 preferably has a distal opening 35 in FIG. 1.

Also, preferably, the apertures are spaced circumferentially and longitudinally such that they are substantially evenly spaced over the distal portion 14 and proximal portion 12 of the tip. In addition preferably, the apertures 20 covered by vent shells 21 extending lengthwise along all proximal 12 and distal portions 14 of suction tip 10 (see FIGS. 1 and 3).

It is desirable that each aperture 20 and vent shell 21 have the same size as the other apertures and shells. The apertures 20 are generally rounded in shape, which is, having a circular border (see FIGS. 4 and 5). It is preferable that each aperture 20 cover by vent shell 21. Each vent shell 21 has spherical shape. However, the vent shells can be oval, triangular, circular, etc., and different sizes, and include (created by) the palatal wall of vent shell 22 and outer wall of vent shell 25. Each shell covered the apertures and created the parietal wall of vent shell 23 in bottom and outer lip of vent shell 24 in the top (see FIGS. 4 and 5).

As shown in FIGS. 1, 3, 6 and 7 the distal portion 14 of the tip 10 has a silicone silicon wedge nozzle 50 surrounding the forward-facing end 11 distal opening 35. The soft silicone rubber forming the silicone wedges nozzle 50 is preferably round in shape or can be oval, triangular, circular, etc. and smooth. This reduces or eliminates patient pain and discomfort due to contact of hard plastic suction with soft tissue of patient.

The given nozzle 50 is formed due to silicone silicon wedges 52 and separated by several slotted openings 51. These slotted openings 51 has shape like vertical milling cutters and they have functions as to improve maximum effectiveness of fluid absorption at least 30 percent more than a similar evacuation tips made from the same material but having no nozzle with wedges and slotted openings, preventing dogging a surgical aspirator and totally removing traumatic absorption of the patient tongue.

An addition silicone wedges 52 and slotted openings 51 located around hollow interior 26 and separated by spaces of outer wall of suction tip 29. The nozzle 50 preferably extends about the entire outer wall perimeter 29 of the distal opening 35.

Figure 3:
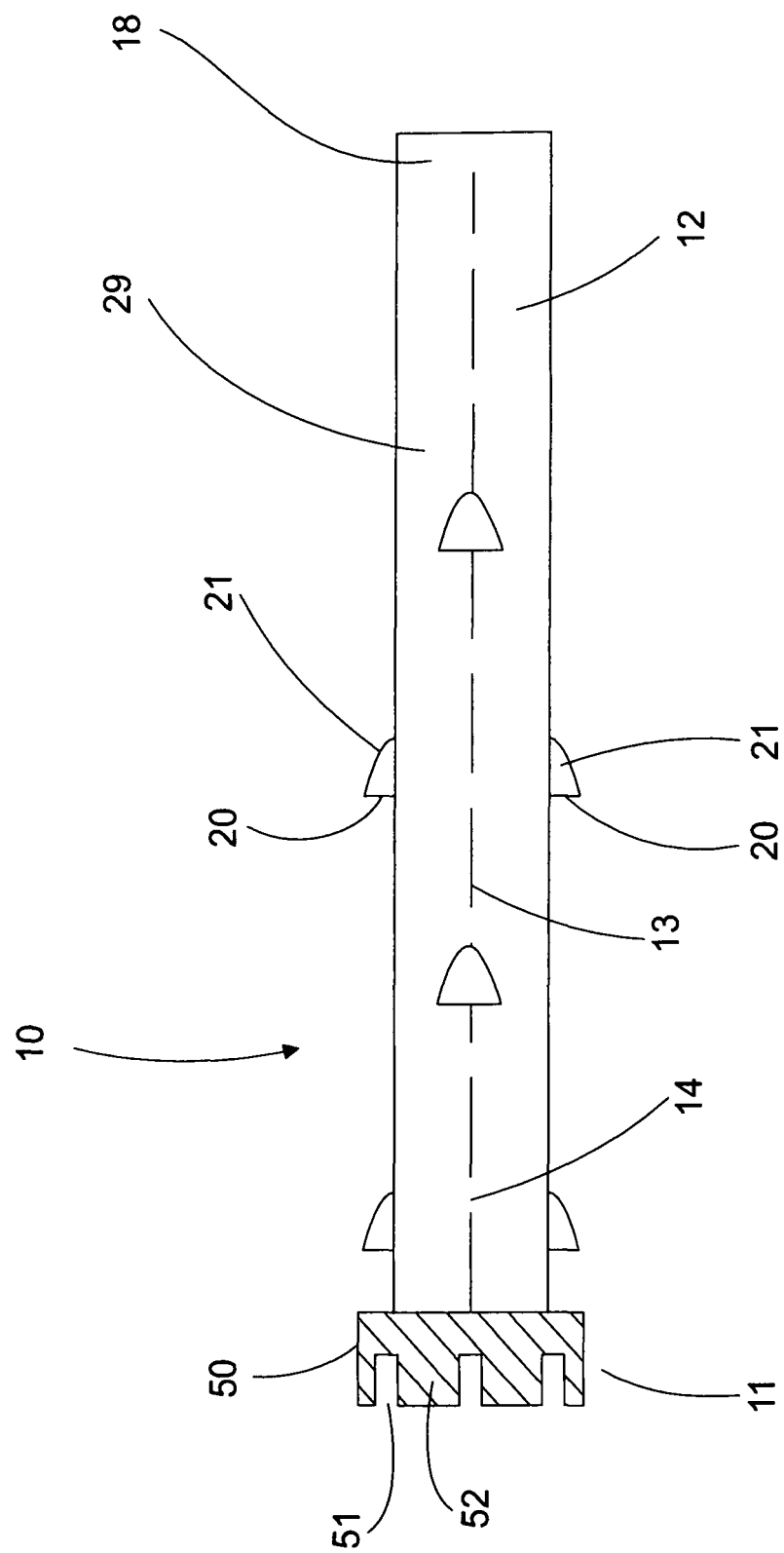
FIG. 3 is a side elevational view of high-volume dental evacuation tip of FIG. 1.
Figure 4:
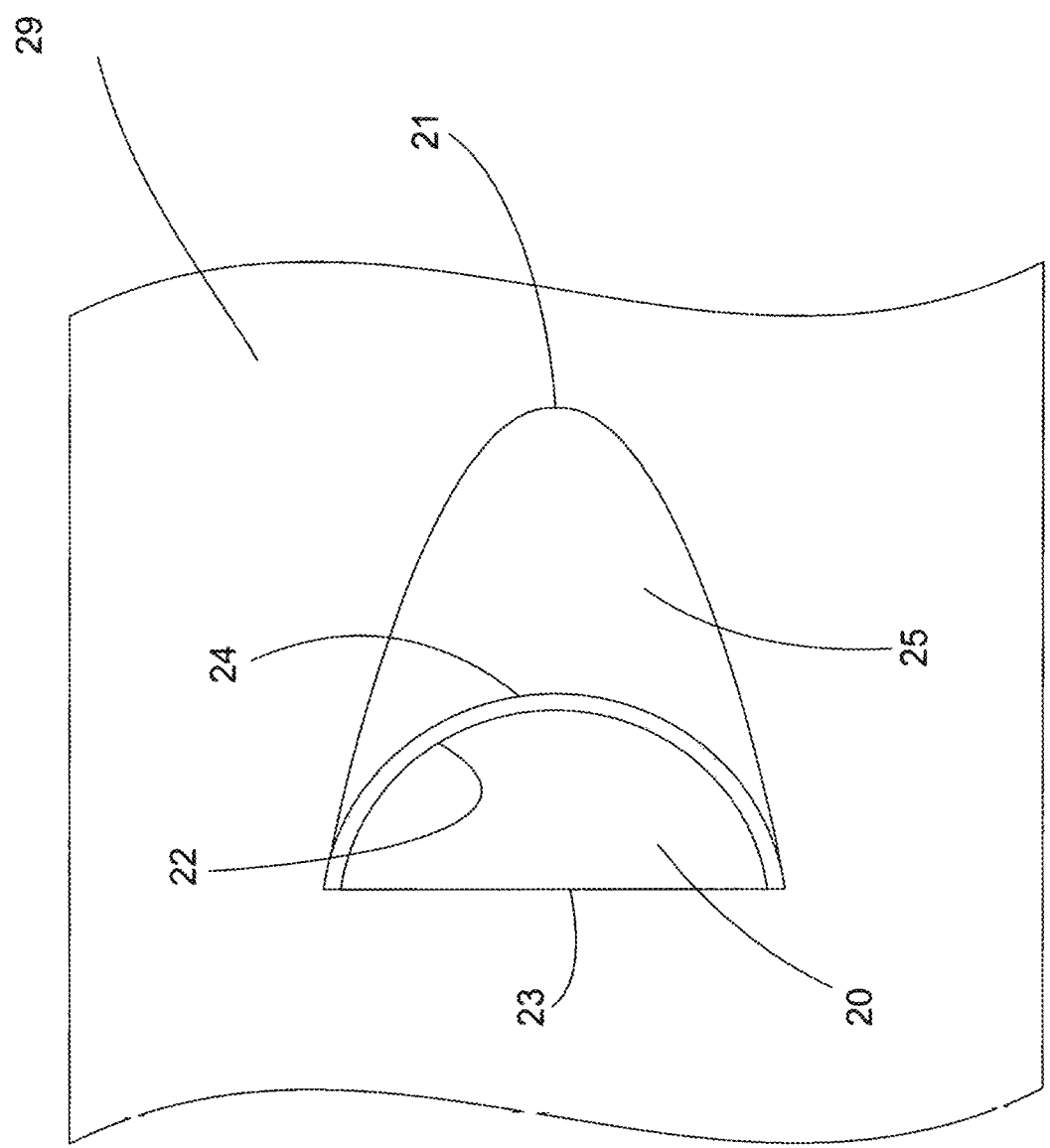
FIG. 4 is a perspective view of a shell as a portion of the high-volume dental evacuation tip of FIG. 1.
Figure 5:
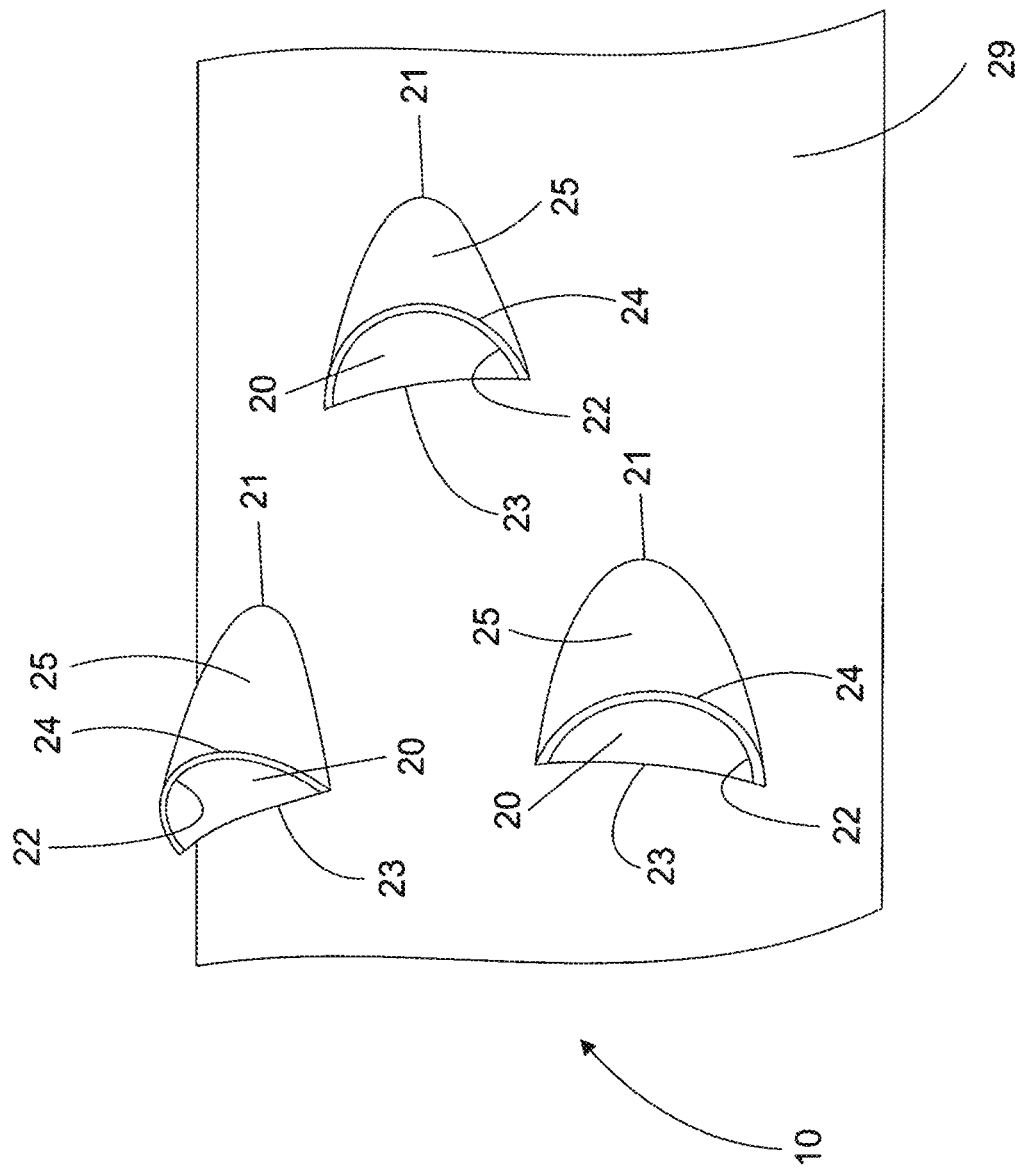
FIG. 5 is a perspective view of a portion of the high-volume dental evacuation tip of FIG. 1.
Figure 6:
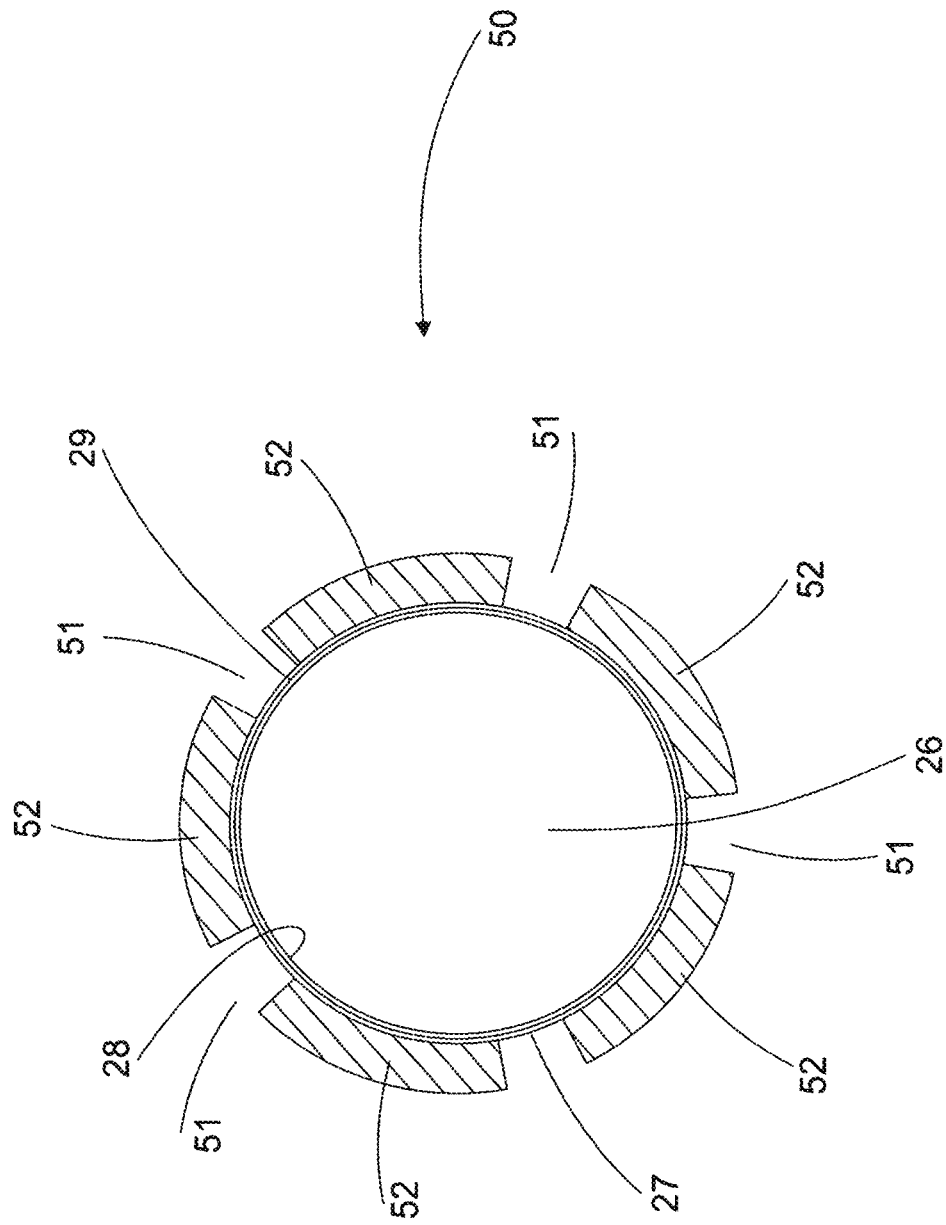
FIG. 6 is a cross-sectional view of the distal portion of tip of the high-volume dental evacuation tip of FIG. 1.

The dental tip 10 is preferably made as one piece and is can made of a workable rigid plastic material such as high density polyethylene or metal. An addition forward facing end 11 made of soft silicone rubber. The soft silicone rubber forming the silicone wedges color 50 (FIGS. 1, 3 and 7).

The dental tip 10 gives the advantage of providing sufficient suction performance during dental procedures compare to different models in the market. The dental tube 10 is ergonomically designed to improve quality and function when used due to the shape of the apertures covered by shells.

Although specific preferred embodiments of the invention have been disclosed in detail for illustrative purposes, it will be recognized that variations and modifications of the disclosed device, including the rearrangement of parts, lie within the scope of the present embodiment.

Suction Efficiency and Impact Force Testing of Comparative Examples

The numerous previous designs were subjected to investigation and tested for suction efficiency and impact force. Analysis of a dental suction tips and its suction capability is investigated for this invention. The analysis was performed to determine the difference of functions in three different designs of dental suctions tips. Following three designs have been selected: standard dental suction tip without apertures, dental suction tip with flat apertures and current invention—with apertures covered by vent shells.

As a preliminary study, a simplified case has been analyzed to investigate the possibility of improving a traditional design. Simplifications include:
two-dimensional geometry
100% air flow (rather than a mixture of air and saliva)
The flow does not necessarily need to be fully accurate to the simulations. However, this report can be viewed as a comparative study—and the results relative to each other show a clear benefit of choosing the current invention with holes covered by vent shells.

Benchmark studies have shown dental equipment reaching pressures between 12-75 kPa. For this simulation, we have assumed the use of an instrument capable of 12 kPa and normal room pressure of 101.3 kPa, creating a pressure difference of 89.3 kPa, which is the force-driven physics in this analysis.

The briefest result of this report is that the current invention with apertures covered by vent shells design is clearly better in two ways; its capability of capturing escaping saliva during operation, as well as its total mass flow capability.

Figure 11:
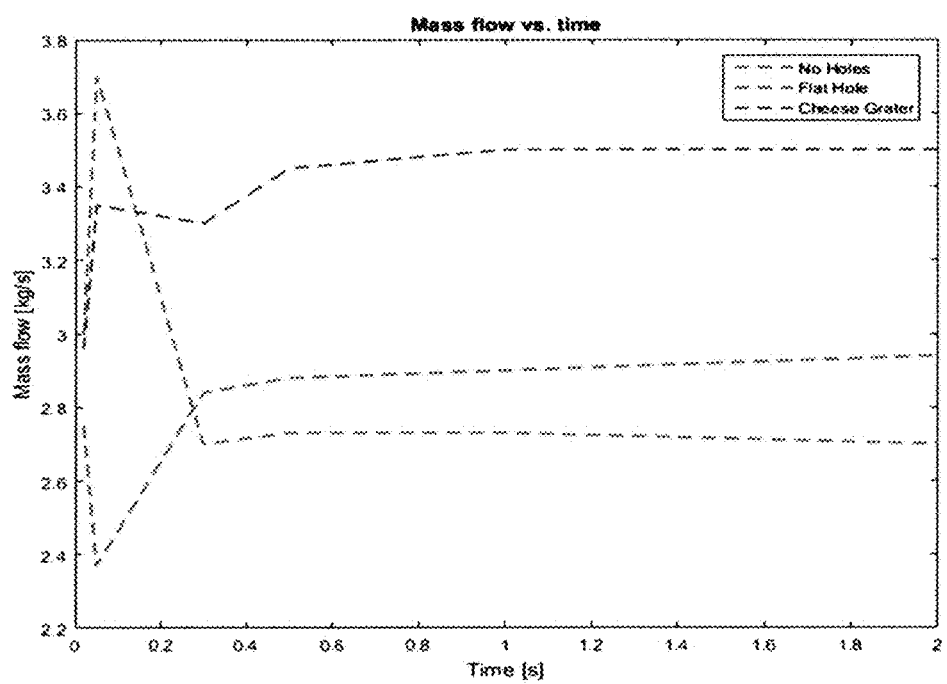
FIG. 11 is a chart of Mass Flow over time for No Holes, Flat Hole, and Cheese Grater embodiments.

For example: try putting the different evacuators in a glass of water and measure the time it takes to empty the glass. The current invention design would finish first, and the flat holes-design would finish last. This is not a trivial conclusion, since one would imagine the dental suction tip with flat holes-design being better than the standard dental suction tip without holes-design. (See FIG. 11).

FIG. 1: Graph showing time-dependent results of mass flow through dental evacuator for different designs.

One can clearly see how the flow is stabilizing after only a few fractions of a second. This is a reasonable behavior for our application.

TABLE 1

Discrete results of mass flow for fully developed flow.

|  | No Hole | Flat Hole | Hole with Shell |
|---|---|---|---|
| Mass flow | 2.94 kg/s | 2.71 kg/s | 3.5 kg/s |

Results below show the suction capability at different time steps. One can see that the results vary a lot in the first half of a second, before stabilizing and reaching a steady flow. This can be compared with the flat section of the graph above. The color represents total velocity in meters per second, where red color is the highest velocity and blue color is the zero velocity.

Figure 8A:
FIG. 8A is a standard suction tip without apertures—suction capability at certain point of time: time 0.05 seconds.
Figure 8B:
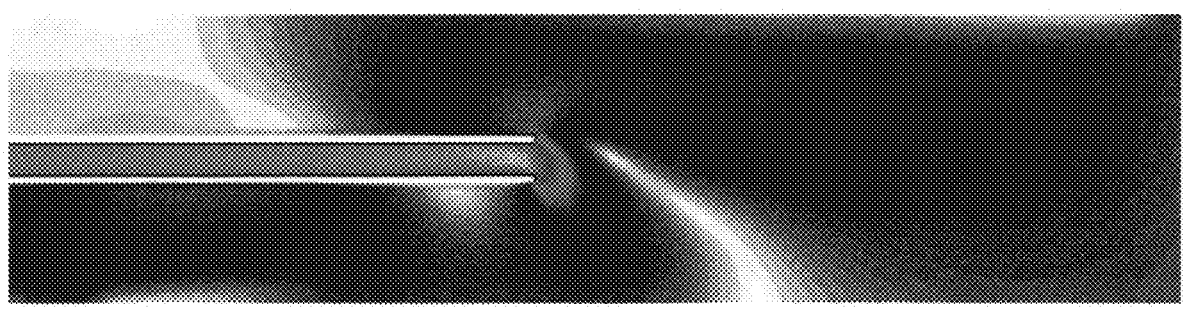
FIG. 8B is a standard suction tip without apertures—suction capability at certain point of time: time 0.1 seconds.
Figure 8C:
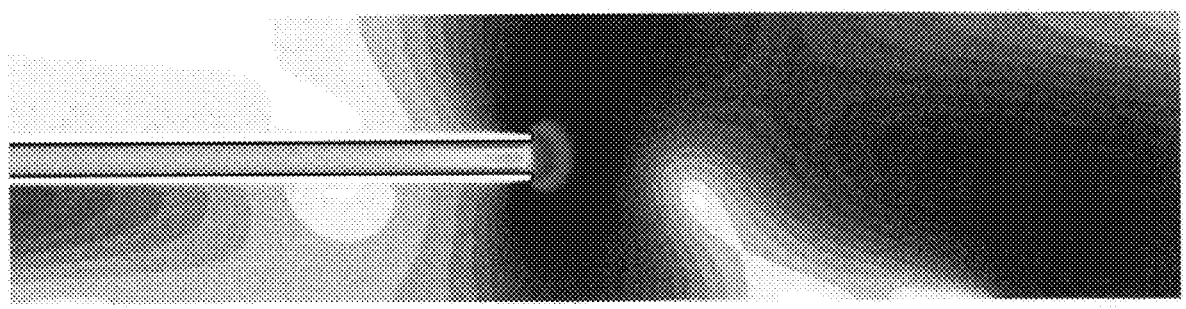
FIG. 8C is a standard suction tip without apertures—suction capability at certain point of time: time 0.2 seconds.
Figure 8D:
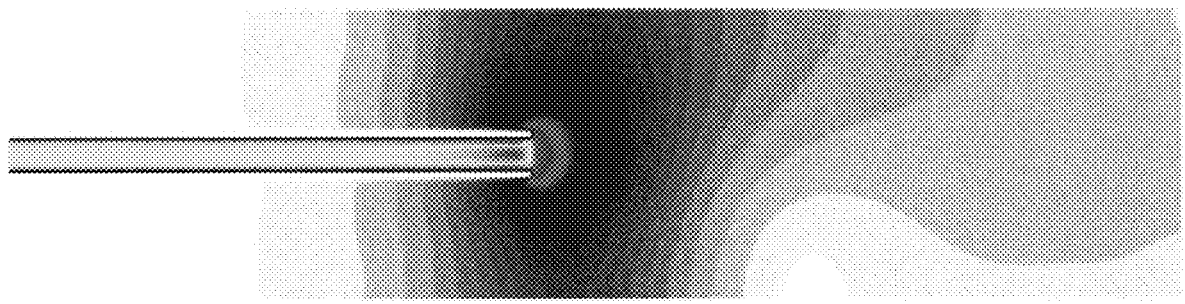
FIG. 8D is a standard suction tip without apertures—suction capability at certain point of time: 0.5 seconds.
Figure 8E:
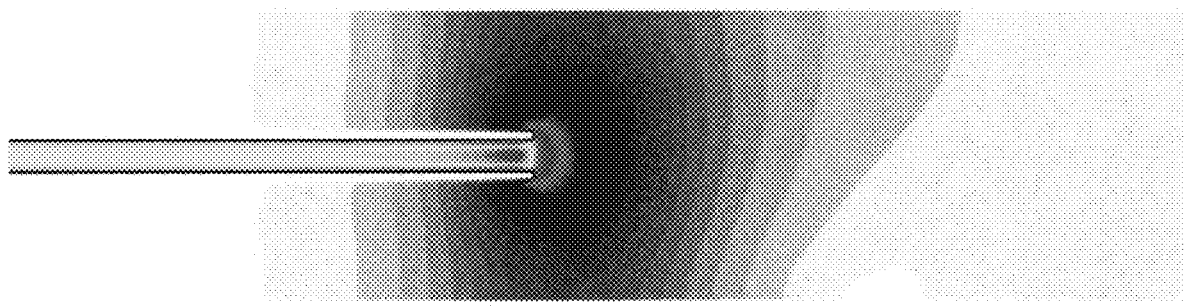
FIG. 8E is a standard suction tip without apertures—suction capability at certain point of time: 1 second.
Figure 8F:
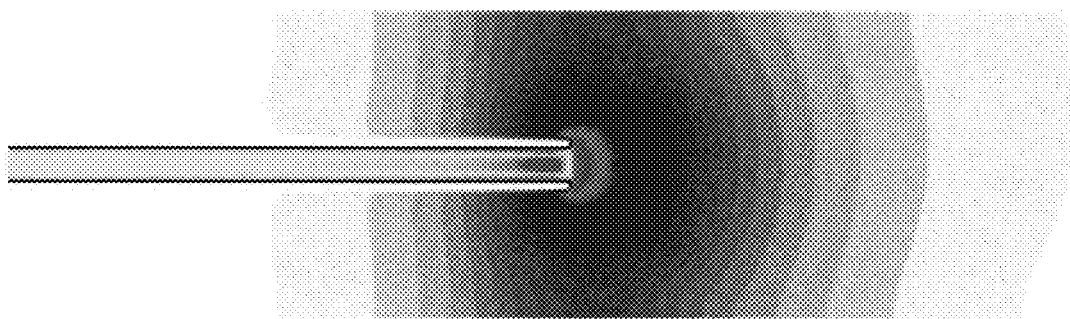
FIG. 8F is a standard suction tip without apertures—suction capability at certain point of time: 2 seconds.
Figure 9A:
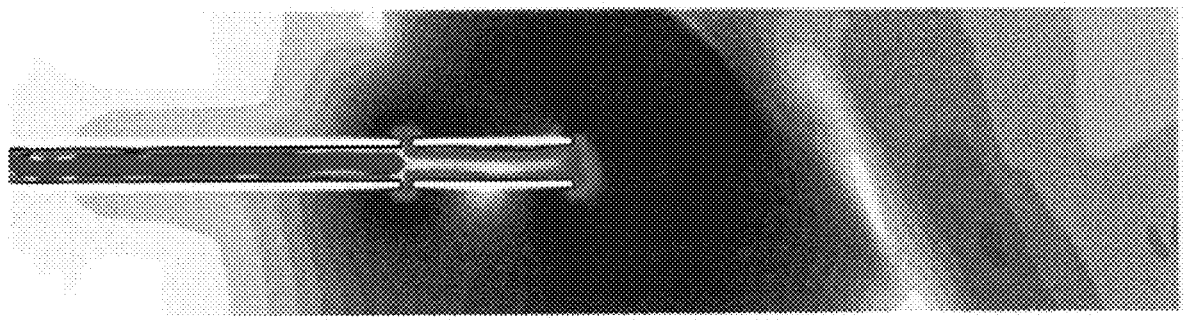
FIG. 9A is a standard suction tip with flat apertures—suction capability at certain point of time: 0.05 seconds.
Figure 9B:
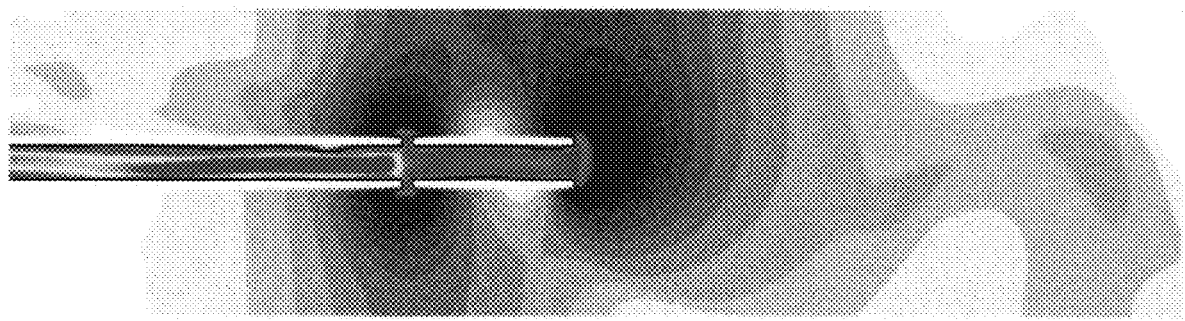
FIG. 9B is a standard suction tip with flat apertures—suction capability at certain point of time: 0.1 seconds.
Figure 9C:
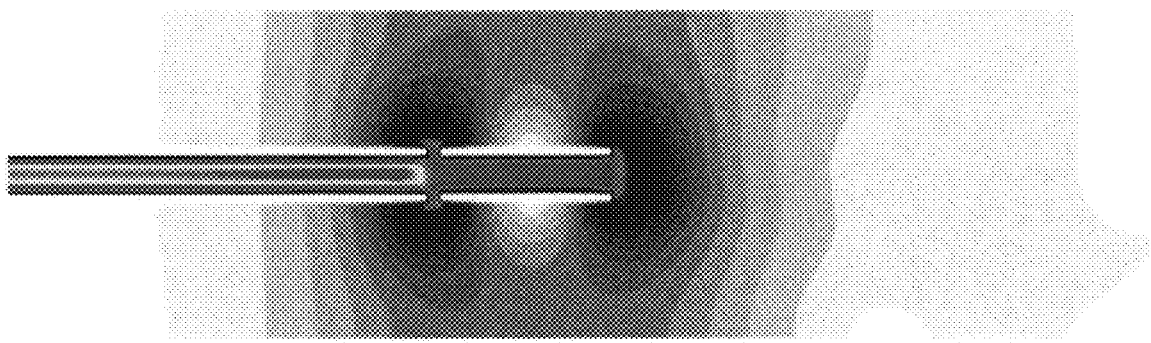
FIG. 9C is a standard suction tip with flat apertures—suction capability at certain point of time: 0.2 seconds.
Figure 9D:
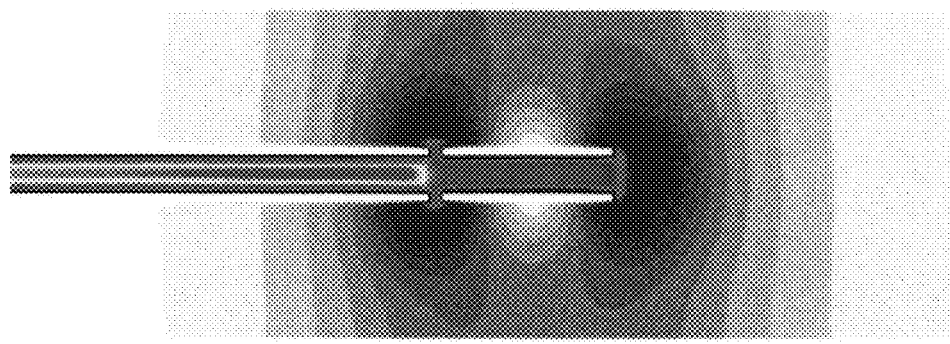
FIG. 9D is a standard suction tip with flat apertures—suction capability at certain point of time: 0.5 seconds.
Figure 9E:
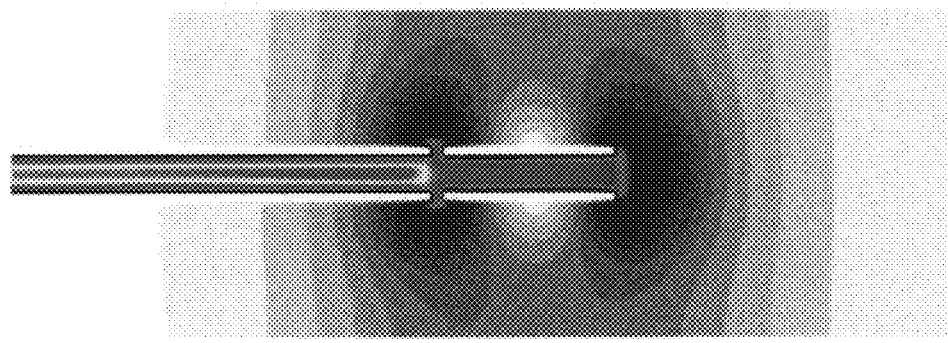
FIG. 9E is a standard suction tip with flat apertures—suction capability at certain point of time: 1 second.
Figure 9F:
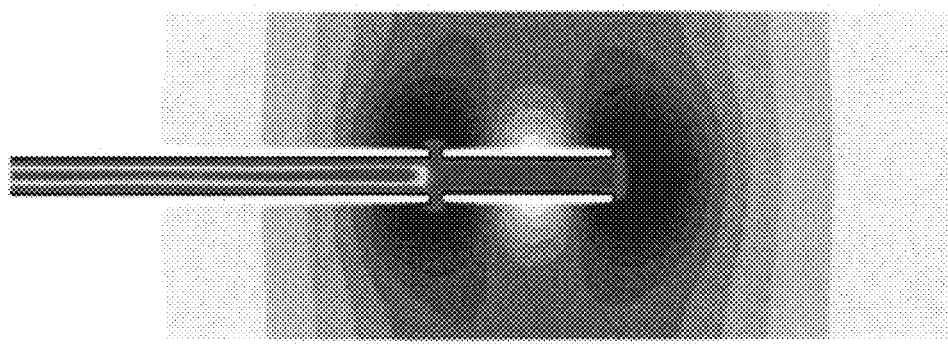
FIG. 9F is a standard suction tip with flat apertures—suction capability at certain point of time: 2 seconds.
Figure 10A:
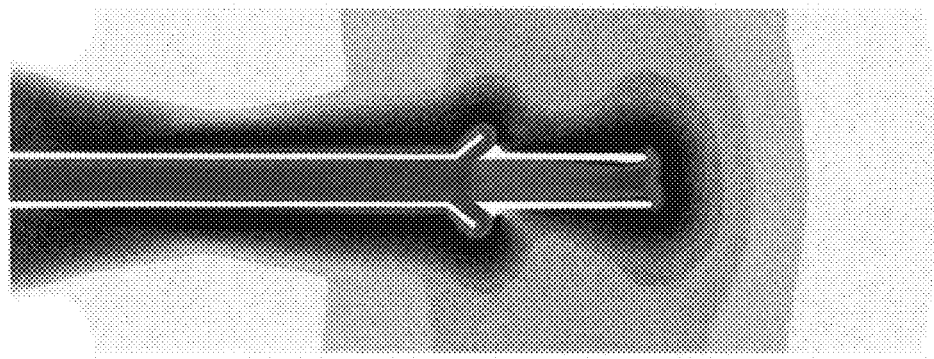
FIG. 10A is a current invention—suction tip with apertures covered by vent shells—suction capability at certain point of time: 0.05 seconds.
Figure 10B:
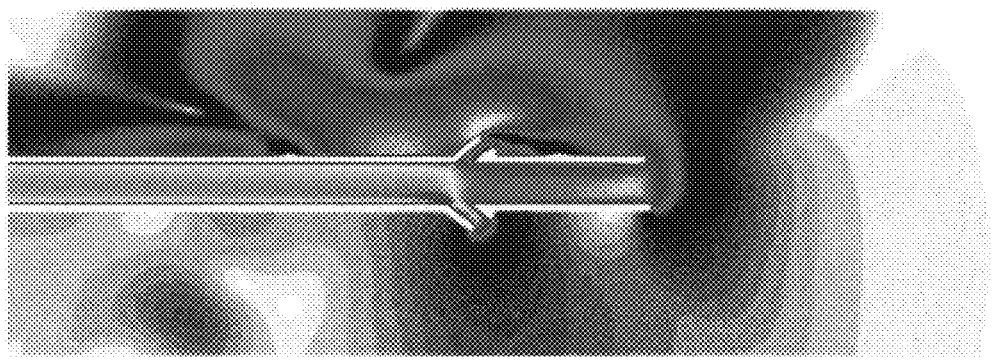
FIG. 10B is a current invention—suction tip with apertures covered by vent shells—suction capability at certain point of time: 0.1 seconds.
Figure 10C:
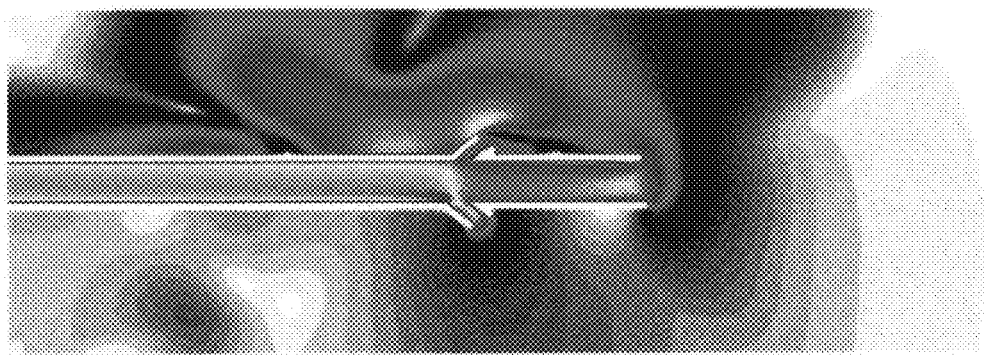
FIG. 10C is a current invention—suction tip with apertures covered by vent shells—suction capability a certain point of time: 0.2 seconds.
Figure 10D:
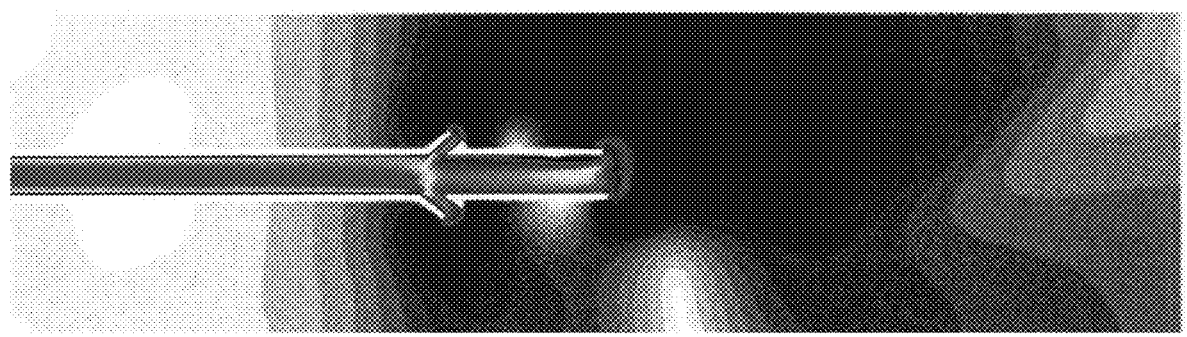
FIG. 10D is a current invention—suction tip with apertures covered by vent shells—suction capability a certain point of time: 0.5 seconds.
Figure 10E:
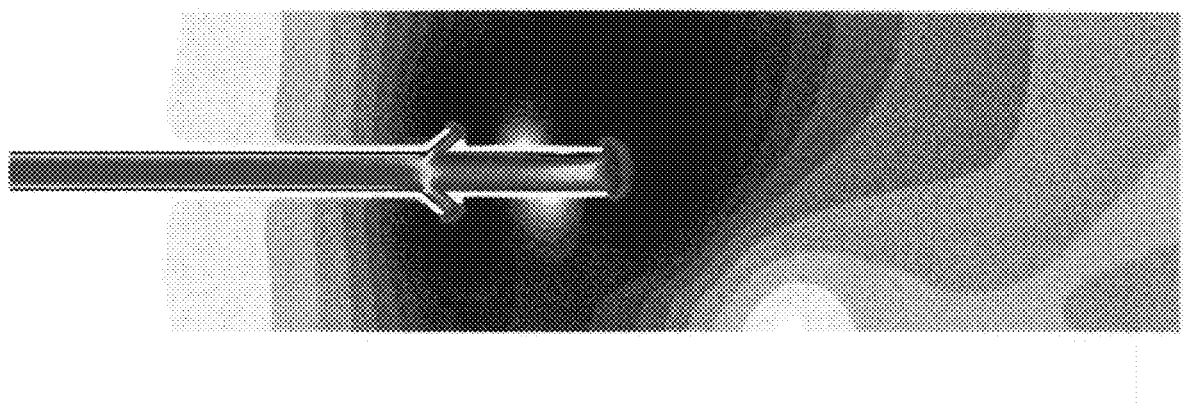
FIG. 10E is a current invention—suction tip with apertures covered by vent shells—suction capability a certain point of time: 1 second.
Figure 10F:
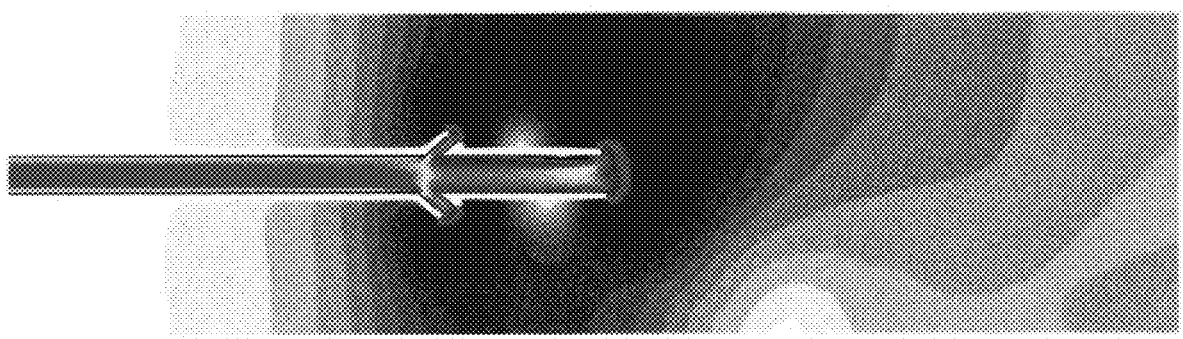
FIG. 10F is a current invention—suction tip with apertures covered by vent shells—suction capability a certain point of time: 2 seconds.

(See FIGS. 8A, 8B, 8C, 8D, 8E, 8F): The Standard suction tip without apertures—suction capability at different time steps:
FIG. 8A: time=0.05 seconds
FIG. 8B: time=0.1 seconds
FIG. 8C: time=0.2 seconds
FIG. 8D: time=0.5 seconds
FIG. 8E: time=1 second
FIG. 8F: time=2 seconds (See FIGS. 9A, 9B, 9C, 9D, 9E, 9F): The Standard suction tip with flat apertures—suction capability at different time steps:
FIG. 9A: time=0.05 seconds
FIG. 9B: time=0.1 seconds
FIG. 9C: time=0.2 seconds
FIG. 9D: time=0.5 seconds
FIG. 9E: time=1 second
FIG. 9F: time=2 seconds FIGS. 10A, 10B, 10C, 10D, 10E, 10F: The current invention—suction tip with apertures covered by vent shells—suction capability at different time steps
FIG. 10A: time=0.05 seconds
FIG. 10B: time=0.1 seconds
FIG. 10C: time=0.2 seconds
FIG. 10D: time=0.5 seconds
FIG. 10E: time=1 second
FIG. 10F: time=2 seconds It can clearly that the current invention suction dental tip with apertures covered by vent shells and soft silicone wedge nozzle.

to be analogous to the commercial design has more suction strong forces of at least 30% more than a similar suction tips made from same material but having no or few flat apertures without went shells.

As noted above current invention providing mass flow for fully developed flow more effective up to 30 percent compared to suction tips without apertures and with limited number of flat apertures respectively.

(See FIGS. 8A, 8B, 8C, 8D, 8E, 8F, 9A, 9B, 9C, 9D, 9E, 9F, 10A, 10B, 10C, 10D, 10E, 10F).

What is claimed is:

1. A high volume dental evacuation tip comprising:
   a proximal end and a distal end wherein an elongated body extends between said proximal end and said distal end along a longitudinal axis;
   said elongated body comprising an outer surface and a hollow interior;
   said proximal end is configured for connection to a suction device;
   said elongated body member including a plurality of functional apertures located along an entire length of said elongated body member, said apertures covered by vent shells; and
   a forward facing end of said distal end of the elongated body member further comprising a silicone wedges nozzle.

2. The high volume dental evacuation tip of claim 1 wherein said elongated body member has a circular cross section.

3. The high volume dental evacuation tip of claim 1 wherein each of said vent shells has spherical shape.

4. The high volume dental evacuation tip of claim 1 wherein said plurality of functional apertures are equally spaced around said entire length said elongated body member.

5. The high volume dental evacuation tip of claim 1 wherein said plurality of functional apertures are rounded in shape.

6. The high volume dental evacuation tip of claim 1 wherein said elongated body is made from one piece of a workable rigid plastic material such as high density polyethylene.

7. A method for evacuating dental fluid from a patient's mouth, the method comprising:
   connecting said proximal end of the high volume dental evacuation tip of claim 1 to a suction source;
   suctioning said dental fluid through said silicone wedges nozzle through said elongated body to the suction source; and
   increasing a suction pressure through said plurality of functional apertures.

8. The method of claim 7 wherein said elongated body member has a circular cross section.

9. The method of claim 7 wherein said vent shells has spherical shape.

10. The method of claim 7 wherein said plurality of functional apertures are equally spaced around said entire length said elongated body member.

11. The method of claim 7 wherein said plurality of functional apertures are rounded in shape.

12. The method of claim 7 wherein said high volume dental evacuation tip is made from one piece of a workable rigid plastic material such as high density polyethylene.

* * * * *